United States Patent [19]

Wuest et al.

[11] Patent Number: 5,274,144

[45] Date of Patent: Dec. 28, 1993

[54] PROCESS FOR THE PRODUCTION OF METAL SOAPS

[75] Inventors: Willi Wuest, Ratingen; Gottfried Duerr, Duesseldorf; Josef Wollmann, Herzogenrath; Harald Liebs, Leverkusen; Hans Scheck, Loxstedt, all of Fed. Rep. of Germany

[73] Assignee: Henkel Kommanditgesellschaft auf Aktien, Duesseldorf, Fed. Rep. of Germany

[21] Appl. No.: 958,311

[22] PCT Filed: Jun. 6, 1991

[86] PCT No.: PCT/EP91/01051

§ 371 Date: Feb. 16, 1993

§ 102(e) Date: Feb. 16, 1993

[87] PCT Pub. No.: WO91/19691

PCT Pub. Date: Dec. 26, 1991

[30] Foreign Application Priority Data

Jun. 15, 1990 [DE] Fed. Rep. of Germany ....... 4019167

[51] Int. Cl.$^5$ .................. C07C 51/00; C07C 53/126; C07C 51/41
[52] U.S. Cl. .................. 554/156; 554/71; 554/73; 554/75; 554/157; 528/935
[58] Field of Search .............. 554/71, 73, 75, 156, 554/157; 426/601, 623, 630, 807, 74; 528/935

[56] References Cited

U.S. PATENT DOCUMENTS

| | | | |
|---|---|---|---|
| 3,367,869 | 2/1968 | Silver et al. | 554/75 X |
| 3,787,160 | 1/1974 | Leister | 425/208 |
| 4,029,682 | 6/1977 | Foulks, Jr. | 554/71 X |
| 4,316,852 | 2/1982 | Blachford | 554/71 X |
| 4,826,694 | 5/1989 | McAskie | 426/74 |
| 4,927,548 | 5/1990 | Hirsch et al. | 252/17 |
| 5,191,098 | 3/1993 | Koenig et al. | 554/156 |

FOREIGN PATENT DOCUMENTS

| | | |
|---|---|---|
| 0163395 | 12/1985 | European Pat. Off. . |
| 0304831 | 3/1989 | European Pat. Off. . |
| 0330097 | 8/1989 | European Pat. Off. . |
| 1544697 | 2/1970 | Fed. Rep. of Germany . |
| 1545697 | 11/1973 | Fed. Rep. of Germany . |
| 1794429 | 11/1979 | Fed. Rep. of Germany . |
| 3806192 | 9/1989 | Fed. Rep. of Germany . |
| 2113521 | 8/1983 | United Kingdom . |

*Primary Examiner*—Arthur C. Prescott
*Attorney, Agent, or Firm*—Ernest G. Szoke; Wayne C. Jaeschke; Daniel S. Ortiz

[57] ABSTRACT

A process for the production of a solid metal soap of the formula $$M(R-COO)(R''-COO)$$

in which M is at least one metal from the group of Ca, Mg, Cd, Ba, Zn, and Pb; and R and R' are $C_8$-$C_{34}$ hydrocarbon radicals, by direct synthesis from at least one fatty acid with metal oxides and/or metal hydroxides which comprises maintaining a reaction zone containing a liquid phase comprising fatty acid under reduced pressure, passing a portion of the liquid phase to an external premixing zone, introducing a solid metal oxide and/or metal hydroxide into the liquid phase in the premixing zone, passing the mixture to the reaction zone through an intensive mixing zone, and continuously removing water of neutralization formed by the reaction.

22 Claims, No Drawings

PROCESS FOR THE PRODUCTION OF METAL SOAPS

FIELD OF THE INVENTION

This invention relates to a process for the production of solid, neutral or basic metal soaps by a controlled solid/liquid reaction of liquid fatty acids with solid metal oxides and/or metal hydroxides in an external premixing zone under reduced pressure and to the use of the metal salts as a stabilizer and/or lubricant mixture in the processing of plastics.

BACKGROUND OF THE INVENTION

It is known that metal soaps are produced either by the melt process, in which the molten fatty acid is reacted with metal oxides, hydroxides and/or suitable metal salts, or by the precipitation process in which their sodium soaps are subjected to double decomposition with water-soluble salts of the corresponding metals. The precipitation process generally gives very clean and voluminous products which can be processed at temperatures below 100° C. However, filtration and drying costs make it much more expensive than the melt process.

Stabilizers produced by the melt process are satisfactory in purity and color for many industrial applications, for example as stabilizers in the processing of plastics. For example, the lead, barium and cadmium compounds have been successfully used in practice as such stabilizers. However, these substances have a highly toxic effect, particularly when they are present in powder form. Dust emission, particularly during processing, is a particular hazard to manufacturers of powder-form stabilizers because the powder-form metal soaps are taken up by the respiratory system and are able to develop their toxic effect therein.

RELATED ART

For these reasons, melt processes are described in DE-PS 15 44 697 and DE-PS 17 94 429 which, to prevent dust emission, claim a stabilizer/lubricant combination consisting of a mixture—combined in the melt—of a purely organic component suitable as lubricant, for example an ester of wax acids and higher aliphatic alcohols, paraffins or fatty alcohols, a suitable metal soap, a long-chain aliphatic carboxylic acid or basic lead salts of inorganic or organic acids. DE-PS 15 45 697 in particular describes a process for the production of these dust-free stabilizer/lubricant combinations, in which the toxic, insoluble dust-form stabilizers are dispersed in melts of the lubricants or in molten mixtures of stabilizers and lubricants and are converted into the solid state either on a flake-forming roller or by simple discharge into pans. The powder-form toxic stabilizers are completely enveloped in the non-toxic lubricants by this process. They are present in solid form and are completely dust-free because the lubricants naturally have considerably better adhesion than the powder-form stabilizers.

In addition, EP-A 163 395 and GB-A 2,113,521 describe processes for the production of animals feeds in which liquid or molten fatty acids are reacted with calcium oxide or calcium hydroxide in the presence of proteins and carbohydrates. However, these processes are very expensive on equipment because the reaction mixture, which evidently does not react off completely, has to be spread out on an endless belt or the like for after-reaction and drying. The calcium soaps obtained in this process would appear to be difficult to convert into free-flowing particles without the additives mentioned above, such as proteins or carbohydrates.

Finally, applicants' DE-OS 38 06 192 describes a process for the production of powder-form basic metal soaps, in which powder-form fatty acids are reacted with powder-form metal oxides or metal oxide mixtures in the presence of water or an acid as catalyst at temperatures from ambient temperature to 100° C., optionally under reduced pressure, the reaction mixture having to be present throughout the reaction in the form of discrete free-flowing particles.

Now, the problem addressed by the present invention was to provide an improved process for the production of powder-form, neutral or basic metal soaps which would provide for dust-free, environmentally safe introduction of the solid metal oxide or metal hydroxide into the fatty acid melt in the form of a controlled solid/liquid reaction without the addition of a catalyst. Another problem addressed by the present invention was to provide a process for working up the liquid metal soaps which would enable the water of neutralization formed to be readily removed under process conditions via a suitable condensation unit.

BRIEF DESCRIPTION OF THE INVENTION

The technical solution to the problem addressed by the present invention is based on the concept of removing parts of the fluid phase of the fatty acid mixture initially introduced from the contents of the reactor under process conditions and delivering them to a premixing zone into which the solid metal oxide and/or hydroxide is introduced. In this premixing zone, a mixture is formed from the circulated liquid phase and the solid phase introduced and is adjusted in its consistency so that the mixture may function as a so-called "living seal". By establishing suitable reaction conditions for the solid reactants to be introduced into the interior of the reactor kept under reduced pressure, the pressure inside the reactor can be reliably controlled with regard to foaming. After the solid has been introduced, the reaction space of the premixing zone can be closed by suitable mechanical elements so that outside air cannot be admitted into the reaction system.

Accordingly, the present invention relates to a process for the production of solid, neutral or basic metal soaps corresponding to the following general formula

$$M(R-COO)(R^1-COO)$$

in which M represent one or more metal cations from the group consisting of Ca, Mg, Cd, Ba, Zn and Pb and R and $R^1$ may be the same or different and represent $C_{8-34}$ hydrocarbon radicals, by direct synthesis from a corresponding fatty acid or fatty acid mixture with metal oxides and/or metal hydroxides, characterized in that a stream of the liquid phase of a fatty acid or fatty acid mixture kept under reduced pressure in the reactor is run off into an external premixing zone and contacted therein with a solid metal oxide and/or metal hydroxide in a solid/liquid reaction, the reaction product formed is returned to the reactor via a following intensive mixer and the water of neutralization formed is continuously removed from the reactor via the gas phase.

The advantages of the process according to the invention lie on the one hand in the exact dust-free and, hence, environmentally safe introduction of the metal oxides or metal hydroxides into the fatty acid melt, so that the reactor capacity can be better utilized through relatively low foaming, and on the other hand in the fact that, in contrast to the prior art, there is no need to add a catalyst. Another advantage of the process according to the invention is that the metal soaps returned to the reactor do not have to be subjected to a time-consuming after-reaction because the neutralization reaction has already taken place completely in the external reaction loop.

DETAILED DESCRIPTION OF THE INVENTION

In one preferred embodiment of the invention, the liquid/solid reaction according to the invention is carried out in such a way that the external premixing zone before the intensive mixer is in direct pressure equalization with the reduced pressure prevailing inside the reactor and at the same time—via the feed system for the solids—with the ambient pressure and the consistency of the paste-form mixture formed in the premixing zone is selected so that the mixture serves as a sealing compound for pressure equalization.

According to the invention, the melt of the fatty acid or fatty acid mixture is run off into the external premixing zone under a reduced internal reactor pressure of approximately 100 to 900 mbar and preferably 200 to 800 mbar, the internal pressure in the premixing zone having to be reduced to take the fall in pressure into consideration. In the premixing zone, the fatty acid melt is contacted under reduced pressure—optionally several times—with at least stoichiometric quantities of metal oxide and/or metal hydroxide in a solid/liquid reaction.

Accordingly, a considerable difference in pressure prevails between the interior of the reactor and the atmospheric pressure. The mixture serving as a "living seal" in the premixing zone therefore has to be adjusted in its consistency so that, under the particular conditions prevailing, it is able to act as an actual sealing element against penetration of the far higher external pressure into the interior of the reactor. This threat to the desired pressure equalization is not the only burden on the paste-form sealing compound. To prepare the mixture, the liquid component has to be introduced into the premixing zone under a limited elevated pressure. If the liquid pressures are too high, parts of the liquid phase are in danger of breaking through the powder-form metal oxide and/or metal hydroxide introduced—preferably continuously—from "outside". Accordingly, this is a second source of danger to the desired trouble-free, preferably continuous section of the process where the solid reactants are introduced into the reactor under time control.

To rule out interruptions of the type just mentioned, a preferred embodiment of the process according to the invention is characterized in that the premixing zone is also operated under reduced pressure. However, the reduced pressures prevailing therein are higher by comparison with the reduced pressure prevailing inside the reactor. The pressure in the premixing zone is preferably kept at around 400 to 900 mbar and, more preferably, at around 750 to 850 mbar. This pressure range is established by adapted control of the streams of liquid and solid material to the premixing zone and their discharge into the interior of the reactor. Selected mass ratios of the streams of liquid and solid reactants have proved to be advantageous for forming the mixture acting as a living seal in the premixing zone. The preferred mass ratios of the liquid phase ($m_1$) to the solid reactants ($m_2$) are in the range from about 20:1 to 100:1. Mass ratios of $m_1$ to $m_2$ of approximately 30:1 to 80:1 have proved to be particularly suitable.

In applicants' above-cited earlier application DE-OS 38 06 192, it is pointed out that the particles should be present in discrete free-flowing form during the reaction. Accordingly, it is proposed (the teaching of the present invention in its preferred embodiment also makes use of this) to subject the mixture of active substances initially formed to fine dispersion under the effect of suitable technical mixing elements. So-called inline mixers, for example operating on the stator/rotor principle, have proved to be particularly suitable for this purpose. More particularly, that unit of the reactor installation which is affected by the process according to the invention is designed, for example, as follows:

A premixing zone is provided separate from the main reaction zone, but in direct pressure communication with the main reaction zone. The dry, preferably powder-form, solid reactant is delivered to the premixing zone, preferably by a screw conveyor. At the same time, liquid phase in admixture with the solid reactant introduced is added to the premixing zone from the interior of the reactor through a circulation pipe so that the mixture acts as a living seal in the premixing zone (particularly in the region of the stated mass ratios of liquid phase to solid phase). From the premixing zone, the paste follows the pressure gradient towards the interior of the reactor and enters the intensive mixer, i.e. for example the following inline mixer, which it then leaves to enter the interior of the reactor. The rate at which the material passes through the premixing zone can be controlled virtually as required under these conditions and optimally adapted to the course of the reaction inside the reactor. The solid reactants may be added in batches and/or continuously.

After the solid reactants have been introduced, the interior of the reactor is closed off from its surroundings. This can be done, for example, by a separating element provided in the premixing zone which separates the premixing zone and the screw conveyor for the solid material from one another. During introduction of the solid reactants, the separating element is opened. After the total quantity of solid reactants required has been added, it is closed again.

In one particularly preferred embodiment of the invention, the solid metal oxide or metal hydroxide is introduced into the fatty acid melt by means of an inline mixer which meters the fatty acid mixture at a rate of approximately 1 to 20 m$^3$ per hour and the solids at a rate of 50 kg to 500 kg per hour and preferably 100 to 300 kg/h. In order to guarantee maximum transport capacity of the inline mixer, the pressure of the installation has to be varied so that the fatty acid melt does not flow back into the space of the screw conveyor for the solid material.

According to the invention, the solid metal oxide and/or metal hydroxide are introduced into the fatty acid melt in such a way that the particle size of the agglomerate formed is below 10 $\mu$m and the acid values of the metal soaps formed are between 0.1 and 30 and preferably between 0.5 and 10.

Any fatty acids of natural or synthetic origin containing 8 to 34 carbon atoms can be converted into the desired powder-form, neutral or basic metal soaps by the process according to the invention, saturated fatty acids preferably being used. The process according to the invention may be used with particular advantage for reacting technical mixtures of natural saturated fatty acids containing 12 to 22 carbon atoms, with the proviso that the melting point of the fatty acids is below 200° C. and preferably below 150° C. Typical examples of such fatty acids are palmitic acid, stearic acid, behenic acid and montanic acids and also technical mixtures rich in the fatty acids mentioned.

According to the invention, oxides and/or hydroxides of calcium, magnesium, cadmium, barium, zinc and/or lead known to the expert may be used as the metal oxides or metal hydroxides. According to the invention, calcium hydroxide, magnesium oxide and/or zinc oxide is/are preferably used. In principle, other salts of the above-mentioned metal ions, such as for example the carbonates, acetates, stearates, or other metal soaps may of course also used in the process according to the invention.

In one preferred embodiment of the invention, diluents adapted to the metal soaps are added to regulate viscosity, particularly where fatty acids having a melting point above 100° to 150° C. are used. Suitable diluents are, for example, paraffins having a melting point of 20° to 150° C. and preferably to 100° C., esters of wax acids and higher aliphatic alcohols preferably containing 12 to 22 carbon atoms, spermaceti or suitable fatty acids. The diluents according to the invention may be mixed with the starting fatty acids in a ratio by weight of 1:10 to 10:1 and preferably 1:2 to 2:1, depending on the metal soap, this ratio by weight being determined by the pumpability of the reactor contents.

To ensure continuous operation of the feeder, it has proved to be advisable for the purposes of the invention to provide the screw with an anti-adhesive coating. This coating is intended to prevent adhesion or bridge formation of the metal oxide or metal hydroxide on the screw conveyor.

The process according to the invention is further optimized by the use of spray cooling in the condensation system. The superheated steam from the neutralization reactor is cooled in the condensation system via an injection nozzle operated with cold process water. Under the effect of this spray cooling, the danger of incrustations being formed in the condensation system is almost completely eliminated and adjustment of the installation pressure remains freely selectable.

The present invention relates to the use of the neutral or basic metal soaps produced by the process according to the invention as stabilizer and/or lubricant mixtures in the processing of plastics and as a feed additive for dairy cows.

The invention is illustrated by the following Examples.

EXAMPLES

Example 1

In a 2.5 m³ reaction vessel equipped with a four-stage MIG stirrer with a base-mounted stirring element and a condensation system, 468 kg technical stearic acid were initially introduced with the bottom outlet valve closed and the jacket heating system was switched on. At a temperature of approximately 70° C., 411 kg glycerol distearate were introduced and the reaction mixture was heated with stirring to 150° C. At the same time, the installation pressure was reduced to 550 mbar. After the bottom outlet valve had been opened, the circulation pump of the external reaction loop and the inline mixer were switched on. By switching on the metering screw and opening the sealing element, 63 kg calcium hydroxide were introduced into the premixing zone over a period of 45 minutes. The transport capacity of the inline mixer was adjusted in such a way that, on the one hand, no excessive foaming was caused by the return of the metal soap via the inline mixer to the reaction vessel and, on the other hand, no fatty acid flowed back into the metering screw. After the solid had been introduced, the installation pressure was reduced to around 30 mbar and the water of neutralization was continuously removed via the condensation system. The end point of the reaction (approx. 1 hour) was determined by continuous sampling and determination of the acid value (required acid value: 5 to 10). The installation pressure was then returned to normal pressure with nitrogen and the liquid reaction mixture was made up in the usual way, for example by prilling. The melting point of the metal soap formed was approximately 95° C. for a yield of 99%.

Example 2

2800 kg technical stearic acid were introduced into and heated to around 95° C. in a 10 m³ reaction vessel equipped in the same way as described in Example 1. 2100 kg of a paraffin wax (melting point: <80° C.) were then introduced over a period of 1 hour with the proviso that a temperature of 85° C. was not exceeded. After the reaction temperature had been increased to 150° C., the installation pressure was lowered to 550 mbar and the external reaction loop was brought into operation via the circulation pump and the inline mixer. 160 kg zinc oxide were then introduced into the inline mixer by the metering screw over a period of 45 minutes. Without any interval, 213 kg calcium hydroxide were introduced in the same way over a period of 35 minutes without any change in the reduced pressure of the system as a whole. After the solid had been introduced, the installation pressure was reduced to around 30 mbar and the water of neutralization was continuously removed through the condensation system. The end point of the reaction (approx. 1 hour) was determined by continuous sampling and determination of the acid value (required acid value: 5 to 10). The installation pressure was then increased to normal pressure with nitrogen and the liquid reaction mixture was made up in the usual way, for example by prilling. The melting point of the metal soap formed was approximately 100° C. for a yield of 99%.

We claim:

1. A process for the production of a solid metal soap of the formula $$M(R-COO)(R''-COO)$$

in which M represents at least one metal cation selected from the group consisting of Ca, Mg, Cd, Ba, Zn, and Pb and R and $R^1$ represent independently selected $C_{8-34}$ hydrocarbon radicals, by direct synthesis from at least one fatty acid with metal oxides and/or metal hydroxides, which comprises: maintaining a reaction zone containing a liquid phase comprising at least one fatty acid under reduced pressure; passing a portion of the liquid phase to an external premixing zone; introducing a solid metal oxide and/or metal hydroxide into the liquid phase in the premix zone to form a mixture; passing this mixture to the reaction zone through an intensive mixing zone; and continuously removing water of neutralization formed by reaction between at least one fatty acid with metal oxides and/or metal hydroxides from the reaction zone as a gas phase.

2. A process of claim 1, wherein the solid/liquid reaction is carried out under conditions wherein the premixing zone is in pressure equalization with the reduced pressure in the reaction zone wherein a paste-form mixture formed in the premixing zone serves as a sealing compound for pressure equalization.

3. A process of claim 1 wherein the pressure in the reaction zone is in the range from 100 to 900 mbar.

4. A process of claim 1 wherein the premixing zone is operated at a reduced internal pressure of 400 to 900 mbar.

5. A process of claim 1 wherein a ratio by weight of the liquid phase to solid phase of 20:1 to 100:1 is maintained in the premixing zone.

6. A process of claim 1 wherein the intensive mixing zone comprises an inline mixer.

7. A process of claim 1 wherein the solid metal oxide and/or metal hydroxide is introduced into the premixing zone by a screw conveyor.

8. A process of claim 1 wherein the at least one fatty acid comprises a mixture of natural fatty acids containing 8 to 34 carbon atoms with the proviso that the melting point of the mixture of fatty acids is below 200° C.

9. A process of claim 1 wherein the metal oxide and/or hydroxide comprises at least one metal oxide or hydroxide selected from the group consisting of calcium hydroxide, magnesium oxide and zinc oxide.

10. A process of claim 1 wherein the liquid phase comprises a diluent to regulate viscosity of the liquid phase.

11. A process of claim 10 wherein the diluent, comprises a paraffin having a melting point of 20° to 150° C. present in relation to the amount of starting fatty acids in a ratio by weight of 1:10 to 10:1.

12. A process of claim 3 wherein the pressure in the reaction zone is in the range of from 200 to 800 mbar.

13. A process of claim 4 wherein the premixing zone is operated at a reduced pressure of from 750 to 850 mbar.

14. A process of claim 8 wherein mixture of fatty acids comprises fatty acids having 12 to 22 carbon atoms.

15. A process of claim 8 wherein the melting point of the mixture of fatty acids is below 150° C.

16. A process of claim 15 wherein the mixture of fatty acids comprises fatty acids having 12 to 22 carbon atoms.

17. A process of claim 11 wherein the diluent has a melting point in the range of 60° C. to 100° C.

18. A process of claim 11 wherein the weight ratio of the diluent to the amount of starting fatty acid is in the range of 1:2 to 2:1.

19. A process of claim 2 wherein the pressure in the reaction zone is in the range of 100 to 900 mbar.

20. A process of claim 19 wherein the pressure in the premixing zone is in the range of 400 to 900 mbar.

21. A method for stabilizing a polymer composition which comprises incorporating in the polymer composition a stability improving amount of a product of the process of claim 1.

22. A method for improving the nutrition of dairy cows which comprises including in feed for dairy cows a product of the process of claim 1.

* * * * *